US009050361B2

(12) United States Patent
Vordermeier et al.

(10) Patent No.: US 9,050,361 B2
(45) Date of Patent: Jun. 9, 2015

(54) DIAGNOSTIC REAGENTS

(75) Inventors: Hans Vordermeier, Weybridge (GB); Adam Whelan, Weybridge (GB)

(73) Assignee: THE SECRETARY OF STATE FOR ENVIRONMENT, FOOD AND RURAL AFFAIRS ACTING THROUGH THE ANIMAL AND PLANT HEALTH AGENCY, Surrey (GB)

( * ) Notice: Subject to any disclaimer, the term of this patent is extended or adjusted under 35 U.S.C. 154(b) by 0 days.

(21) Appl. No.: 13/643,820

(22) PCT Filed: Apr. 28, 2011

(86) PCT No.: PCT/GB2011/050843
§ 371 (c)(1),
(2), (4) Date: Feb. 8, 2013

(87) PCT Pub. No.: WO2011/135369
PCT Pub. Date: Nov. 3, 2011

(65) Prior Publication Data

US 2013/0136699 A1 May 30, 2013

(30) Foreign Application Priority Data

Apr. 28, 2010 (GB) .................................. 1007075.3

(51) Int. Cl.
*A61K 39/04* (2006.01)
*A61K 39/00* (2006.01)
*A61K 49/00* (2006.01)

(52) U.S. Cl.
CPC ............. *A61K 49/0006* (2013.01); *A61K 39/00* (2013.01); *A61K 39/04* (2013.01)

(58) Field of Classification Search
USPC .................. 424/9.1, 9.2, 184.1, 185.1, 234.1, 424/248.1; 530/300, 350
See application file for complete search history.

(56) References Cited

U.S. PATENT DOCUMENTS

| | | | |
|---|---|---|---|
| 2003/0165525 | A1 | 9/2003 | Andersen et al. |
| 2006/0024332 | A1 | 2/2006 | Waters et al. |
| 2007/0054335 | A1 | 3/2007 | Esfandiari et al. |

FOREIGN PATENT DOCUMENTS

| | | |
|---|---|---|
| EP | 2563407 | 3/2013 |
| WO | WO 2009/060184 | 5/2009 |
| WO | WO 2011/135369 | 3/2011 |

OTHER PUBLICATIONS

Sidders et al. Infection and Immunity, vol. 76, No. 9, pp. 3932-3939, Sep. 2008.*
MacGurn, et al. (2005) *Molecular Microbiology* 1653-1663.
Sidders, et al. (2008) *Infection and Immunity* 76(9): 3932-3939.
Manual of Diagnostic Tests and Vaccines for Terrestrial Animals (2009) Chapter 2.4.7 Bovine Tuberculosis, pp. 1-16.
Pollock & Andersen (1997) *The Journal of Infectious Diseases* 175:1251-4.
Whelan, et al., (2003) *Infection and Immunity* 71(11): 6420-6425.
Observations by third parties (Article 115 EPC) from EP Patent Application No. 11721638.2 (Jul. 3, 2013).

* cited by examiner

*Primary Examiner* — Rodney P Swartz
(74) *Attorney, Agent, or Firm* — Hunton & Williams LLP

(57) ABSTRACT

There is provided a skin test diagnostic reagent comprising at least one CFP-10 epitope polypeptide, at least one ESAT-6 epitope polypeptide and at least one Rv3615c epitope polypeptide, the reagent eliciting a positive result when administered in a skin test to an animal infected with *Mycobacterium bovis* or *Mycobacterium tuberculosis*. The reagent is useful in that it can be used in a method to determine whether an animal is infected with *Mycobacterium bovis* or *Mycobacterium tuberculosis*.

21 Claims, 5 Drawing Sheets

SEQUENCE LISTING

```
<160> NUMBER OF SEQ ID NOS: 39

<210> SEQ ID NO 1
<211> LENGTH: 18
<212> TYPE: PRT
<213> ORGANISM: Artificial Sequence
<220> FEATURE:
<223> OTHER INFORMATION: Fragment of full length protein

<400> SEQUENCE: 1

Met Ala Glu Met Lys Thr Asp Ala Ala Thr Leu Ala Gln Glu Ala Gly
1               5                   10                  15

Asn Phe


<210> SEQ ID NO 2
<211> LENGTH: 16
<212> TYPE: PRT
<213> ORGANISM: Artificial Sequence
<220> FEATURE:
<223> OTHER INFORMATION: Fragment of full length protein

<400> SEQUENCE: 2

Gln Glu Ala Gly Asn Phe Glu Arg Ile Ser Gly Asp Leu Lys Thr Gln
1               5                   10                  15


<210> SEQ ID NO 3
<211> LENGTH: 18
<212> TYPE: PRT
<213> ORGANISM: Artificial Sequence
<220> FEATURE:
<223> OTHER INFORMATION: Fragment of full length protein

<400> SEQUENCE: 3

Glu Arg Ile Ser Gly Asp Leu Lys Thr Gln Ile Asp Gln Val Glu Ser
1               5                   10                  15

Thr Ala


<210> SEQ ID NO 4
<211> LENGTH: 17
<212> TYPE: PRT
<213> ORGANISM: Artificial Sequence
<220> FEATURE:
<223> OTHER INFORMATION: Fragment of full length protein
```

<400> SEQUENCE: 4

```
Ile Asp Gln Val Glu Ser Thr Ala Gly Ser Leu Gln Gly Gln Trp Arg
1               5                   10                  15

Gly
```

<210> SEQ ID NO 5
<211> LENGTH: 18
<212> TYPE: PRT
<213> ORGANISM: Artificial Sequence
<220> FEATURE:
<223> OTHER INFORMATION: Fragment of full length protein

<400> SEQUENCE: 5

```
Gly Ser Leu Gln Gly Gln Trp Arg Gly Ala Ala Gly Thr Ala Ala Gln
1               5                   10                  15

Ala Ala
```

<210> SEQ ID NO 6
<211> LENGTH: 18
<212> TYPE: PRT
<213> ORGANISM: Artificial Sequence
<220> FEATURE:
<223> OTHER INFORMATION: Fragment of full length protein

<400> SEQUENCE: 6

```
Ala Gly Thr Ala Ala Gln Ala Ala Val Val Arg Phe Gln Glu Ala Ala
1               5                   10                  15

Asn Lys
```

<210> SEQ ID NO 7
<211> LENGTH: 18
<212> TYPE: PRT
<213> ORGANISM: Artificial Sequence
<220> FEATURE:
<223> OTHER INFORMATION: Fragment of full length protein

<400> SEQUENCE: 7

```
Val Val Arg Phe Gln Glu Ala Ala Asn Lys Gln Lys Gln Glu Leu Asp
1               5                   10                  15

Glu Ile
```

<210> SEQ ID NO 8
<211> LENGTH: 20
<212> TYPE: PRT
<213> ORGANISM: Artificial Sequence
<220> FEATURE:
<223> OTHER INFORMATION: Fragment of full length protein

<400> SEQUENCE: 8

```
Gln Lys Gln Glu Leu Asp Glu Ile Ser Thr Asn Ile Arg Gln Ala Gly
1               5                   10                  15

Val Gln Tyr Ser
            20
```

<210> SEQ ID NO 9
<211> LENGTH: 18
<212> TYPE: PRT
<213> ORGANISM: Artificial Sequence
<220> FEATURE:
<223> OTHER INFORMATION: Fragment of full length protein

<400> SEQUENCE: 9

-continued

Asn Ile Arg Gln Ala Gly Val Gln Tyr Ser Arg Ala Asp Glu Glu Gln
1 5 10 15

Gln Gln

<210> SEQ ID NO 10
<211> LENGTH: 16
<212> TYPE: PRT
<213> ORGANISM: Artificial Sequence
<220> FEATURE:
<223> OTHER INFORMATION: Fragment of full length protein

<400> SEQUENCE: 10

Arg Ala Asp Glu Glu Gln Gln Gln Ala Leu Ser Ser Gln Met Gly Phe
1 5 10 15

<210> SEQ ID NO 11
<211> LENGTH: 16
<212> TYPE: PRT
<213> ORGANISM: Artificial Sequence
<220> FEATURE:
<223> OTHER INFORMATION: Fragment of full length protein

<400> SEQUENCE: 11

Met Thr Glu Gln Gln Trp Asn Phe Ala Gly Ile Glu Ala Ala Ala Ser
1 5 10 15

<210> SEQ ID NO 12
<211> LENGTH: 16
<212> TYPE: PRT
<213> ORGANISM: Artificial Sequence
<220> FEATURE:
<223> OTHER INFORMATION: Fragment of full length protein

<400> SEQUENCE: 12

Ala Gly Ile Glu Ala Ala Ala Ser Ala Ile Gln Gly Asn Val Thr Ser
1 5 10 15

<210> SEQ ID NO 13
<211> LENGTH: 16
<212> TYPE: PRT
<213> ORGANISM: Artificial Sequence
<220> FEATURE:
<223> OTHER INFORMATION: Fragment of full length protein

<400> SEQUENCE: 13

Ala Ile Gln Gly Asn Val Thr Ser Ile His Ser Leu Leu Asp Glu Gly
1 5 10 15

<210> SEQ ID NO 14
<211> LENGTH: 16
<212> TYPE: PRT
<213> ORGANISM: Artificial Sequence
<220> FEATURE:
<223> OTHER INFORMATION: Fragment of full length protein

<400> SEQUENCE: 14

Ile His Ser Leu Leu Asp Glu Gly Lys Gln Ser Leu Thr Lys Leu Ala
1 5 10 15

<210> SEQ ID NO 15
<211> LENGTH: 16
<212> TYPE: PRT
<213> ORGANISM: Artificial Sequence
<220> FEATURE:
<223> OTHER INFORMATION: Fragment of full length protein

<400> SEQUENCE: 15

Lys Gln Ser Leu Thr Lys Leu Ala Ala Ala Trp Gly Gly Ser Gly Ser
1 5 10 15

<210> SEQ ID NO 16
<211> LENGTH: 16
<212> TYPE: PRT
<213> ORGANISM: Artificial Sequence
<220> FEATURE:
<223> OTHER INFORMATION: Fragment of full length protein

<400> SEQUENCE: 16

Ala Ala Trp Gly Gly Ser Gly Ser Glu Ala Tyr Gln Gly Val Gln Gln
1 5 10 15

<210> SEQ ID NO 17
<211> LENGTH: 16
<212> TYPE: PRT
<213> ORGANISM: Artificial Sequence
<220> FEATURE:
<223> OTHER INFORMATION: Fragment of full length protein

<400> SEQUENCE: 17

Glu Ala Tyr Gln Gly Val Gln Gln Lys Trp Asp Ala Thr Ala Thr Glu
1 5 10 15

<210> SEQ ID NO 18
<211> LENGTH: 16
<212> TYPE: PRT
<213> ORGANISM: Artificial Sequence
<220> FEATURE:
<223> OTHER INFORMATION: Fragment of full length protein

<400> SEQUENCE: 18

Lys Trp Asp Ala Thr Ala Thr Glu Leu Asn Asn Ala Leu Gln Asn Leu
1 5 10 15

<210> SEQ ID NO 19
<211> LENGTH: 16
<212> TYPE: PRT
<213> ORGANISM: Artificial Sequence
<220> FEATURE:
<223> OTHER INFORMATION: Fragment of full length protein

<400> SEQUENCE: 19

Leu Asn Asn Ala Leu Gln Asn Leu Ala Arg Thr Ile Ser Glu Ala Gly
1 5 10 15

<210> SEQ ID NO 20
<211> LENGTH: 16
<212> TYPE: PRT
<213> ORGANISM: Artificial Sequence
<220> FEATURE:
<223> OTHER INFORMATION: Fragment of full length protein

<400> SEQUENCE: 20

Ala Arg Thr Ile Ser Glu Ala Gly Gln Ala Met Ala Ser Thr Glu Gly
1 5 10 15

<210> SEQ ID NO 21
<211> LENGTH: 15
<212> TYPE: PRT
<213> ORGANISM: Artificial Sequence
<220> FEATURE:
<223> OTHER INFORMATION: Fragment of full length protein

<400> SEQUENCE: 21

-continued

Gln Ala Met Ala Ser Thr Glu Gly Asn Val Thr Gly Met Phe Ala
1 5 10 15

<210> SEQ ID NO 22
<211> LENGTH: 20
<212> TYPE: PRT
<213> ORGANISM: Artificial Sequence
<220> FEATURE:
<223> OTHER INFORMATION: Fragment of full length protein

<400> SEQUENCE: 22

Gly Leu Val Cys Gly Gly Val His Thr Ala Asn Ala Thr Val Tyr Met
1 5 10 15

Ile Asp Thr Val
20

<210> SEQ ID NO 23
<211> LENGTH: 20
<212> TYPE: PRT
<213> ORGANISM: Artificial Sequence
<220> FEATURE:
<223> OTHER INFORMATION: Fragment of full length protein

<400> SEQUENCE: 23

Met Thr Glu Asn Leu Thr Val Gln Pro Glu Arg Leu Gly Val Leu Ala
1 5 10 15

Ser His His Asp
20

<210> SEQ ID NO 24
<211> LENGTH: 20
<212> TYPE: PRT
<213> ORGANISM: Artificial Sequence
<220> FEATURE:
<223> OTHER INFORMATION: Fragment of full length protein

<400> SEQUENCE: 24

Pro Glu Arg Leu Gly Val Leu Ala Ser His His Asp Asn Ala Ala Val
1 5 10 15

Asp Ala Ser Ser
20

<210> SEQ ID NO 25
<211> LENGTH: 20
<212> TYPE: PRT
<213> ORGANISM: Artificial Sequence
<220> FEATURE:
<223> OTHER INFORMATION: Fragment of full length protein

<400> SEQUENCE: 25

Ser His His Asp Asn Ala Ala Val Asp Ala Ser Ser Gly Val Glu Ala
1 5 10 15

Ala Ala Gly Leu
20

<210> SEQ ID NO 26
<211> LENGTH: 20
<212> TYPE: PRT
<213> ORGANISM: Artificial Sequence
<220> FEATURE:
<223> OTHER INFORMATION: Fragment of full length protein

<400> SEQUENCE: 26

Asp Ala Ser Ser Gly Val Glu Ala Ala Ala Gly Leu Gly Glu Ser Val
1 5 10 15

Ala Ile Thr His
20

<210> SEQ ID NO 27
<211> LENGTH: 20
<212> TYPE: PRT
<213> ORGANISM: Artificial Sequence
<220> FEATURE:
<223> OTHER INFORMATION: Fragment of full length protein

<400> SEQUENCE: 27

Ala Ala Gly Leu Gly Glu Ser Val Ala Ile Thr His Gly Pro Tyr Cys
1 5 10 15

Ser Gln Phe Asn
20

<210> SEQ ID NO 28
<211> LENGTH: 20
<212> TYPE: PRT
<213> ORGANISM: Artificial Sequence
<220> FEATURE:
<223> OTHER INFORMATION: Fragment of full length protein

<400> SEQUENCE: 28

Ala Ile Thr His Gly Pro Tyr Cys Ser Gln Phe Asn Asp Thr Leu Asn
1 5 10 15

Val Tyr Leu Thr
20

<210> SEQ ID NO 29
<211> LENGTH: 20
<212> TYPE: PRT
<213> ORGANISM: Artificial Sequence
<220> FEATURE:
<223> OTHER INFORMATION: Fragment of full length protein

<400> SEQUENCE: 29

Ser Gln Phe Asn Asp Thr Leu Asn Val Tyr Leu Thr Ala His Asn Ala
1 5 10 15

Leu Gly Ser Ser
20

<210> SEQ ID NO 30
<211> LENGTH: 20
<212> TYPE: PRT
<213> ORGANISM: Artificial Sequence
<220> FEATURE:
<223> OTHER INFORMATION: Fragment of full length protein

<400> SEQUENCE: 30

Val Tyr Leu Thr Ala His Asn Ala Leu Gly Ser Ser Leu His Thr Ala
1 5 10 15

Gly Val Asp Leu
20

<210> SEQ ID NO 31
<211> LENGTH: 20
<212> TYPE: PRT
<213> ORGANISM: Artificial Sequence
<220> FEATURE:
<223> OTHER INFORMATION: Fragment of full length protein

<400> SEQUENCE: 31

Leu Gly Ser Ser Leu His Thr Ala Gly Val Asp Leu Ala Lys Ser Leu 1 5 10 15

Arg Ile Ala Ala
20

<210> SEQ ID NO 32
<211> LENGTH: 20
<212> TYPE: PRT
<213> ORGANISM: Artificial Sequence
<220> FEATURE:
<223> OTHER INFORMATION: Fragment of full length protein

<400> SEQUENCE: 32

Gly Val Asp Leu Ala Lys Ser Leu Arg Ile Ala Ala Lys Ile Tyr Ser
1 5 10 15

Glu Ala Asp Glu
20

<210> SEQ ID NO 33
<211> LENGTH: 20
<212> TYPE: PRT
<213> ORGANISM: Artificial Sequence
<220> FEATURE:
<223> OTHER INFORMATION: Fragment of full length protein

<400> SEQUENCE: 33

Arg Ile Ala Ala Lys Ile Tyr Ser Glu Ala Asp Glu Ala Trp Arg Lys
1 5 10 15

Ala Ile Asp Gly
20

<210> SEQ ID NO 34
<211> LENGTH: 20
<212> TYPE: PRT
<213> ORGANISM: Artificial Sequence
<220> FEATURE:
<223> OTHER INFORMATION: Fragment of full length protein

<400> SEQUENCE: 34

Ala Lys Ile Tyr Ser Glu Ala Asp Glu Ala Trp Arg Lys Ala Ile Asp
1 5 10 15

Gly Leu Phe Thr
20

<210> SEQ ID NO 35
<211> LENGTH: 100
<212> TYPE: PRT
<213> ORGANISM: Mycobacterium bovis

<400> SEQUENCE: 35

Met Ala Glu Met Lys Thr Asp Ala Ala Thr Leu Ala Gln Glu Ala Gly
1 5 10 15

Asn Phe Glu Arg Ile Ser Gly Asp Leu Lys Thr Gln Ile Asp Gln Val
20 25 30

Glu Ser Thr Ala Gly Ser Leu Gln Gly Gln Trp Arg Gly Ala Ala Gly
35 40 45

Thr Ala Ala Gln Ala Ala Val Val Arg Phe Gln Glu Ala Ala Asn Lys
50 55 60

Gln Lys Gln Glu Leu Asp Glu Ile Ser Thr Asn Ile Arg Gln Ala Gly
65 70 75 80

Val Gln Tyr Ser Arg Ala Asp Glu Glu Gln Gln Gln Ala Leu Ser Ser
85 90 95

Gln Met Gly Phe
100

<210> SEQ ID NO 36
<211> LENGTH: 95
<212> TYPE: PRT
<213> ORGANISM: Mycobacterium bovis

<400> SEQUENCE: 36

Met Thr Glu Gln Gln Trp Asn Phe Ala Gly Ile Glu Ala Ala Ala Ser
1 5 10 15

Ala Ile Gln Gly Asn Val Thr Ser Ile His Ser Leu Leu Asp Glu Gly
20 25 30

Lys Gln Ser Leu Thr Lys Leu Ala Ala Ala Trp Gly Gly Ser Gly Ser
35 40 45

Glu Ala Tyr Gln Gly Val Gln Gln Lys Trp Asp Ala Thr Ala Thr Glu
50 55 60

Leu Asn Asn Ala Leu Gln Asn Leu Ala Arg Thr Ile Ser Glu Ala Gly
65 70 75 80

Gln Ala Met Ala Ser Thr Glu Gly Asn Val Thr Gly Met Phe Ala
85 90 95

<210> SEQ ID NO 37
<211> LENGTH: 220
<212> TYPE: PRT
<213> ORGANISM: Mycobacterium bovis

<400> SEQUENCE: 37

Met Ile Asn Val Gln Ala Lys Pro Ala Ala Ala Ala Ser Leu Ala Ala
1 5 10 15

Ile Ala Ile Ala Phe Leu Ala Gly Cys Ser Ser Thr Lys Pro Val Ser
20 25 30

Gln Asp Thr Ser Pro Lys Pro Ala Thr Ser Pro Ala Ala Pro Val Thr
35 40 45

Thr Ala Ala Met Ala Asp Pro Ala Ala Asp Leu Ile Gly Arg Gly Cys
50 55 60

Ala Gln Tyr Ala Ala Gln Asn Pro Thr Gly Pro Gly Ser Val Ala Gly
65 70 75 80

Met Ala Gln Asp Pro Val Ala Thr Ala Ala Ser Asn Asn Pro Met Leu
85 90 95

Ser Thr Leu Thr Ser Ala Leu Ser Gly Lys Leu Asn Pro Asp Val Asn
100 105 110

Leu Val Asp Thr Leu Asn Gly Gly Glu Tyr Thr Val Phe Ala Pro Thr
115 120 125

Asn Ala Ala Phe Asp Lys Leu Pro Ala Ala Thr Ile Asp Gln Leu Lys
130 135 140

Thr Asp Ala Lys Leu Leu Ser Ser Ile Leu Thr Tyr His Val Ile Ala
145 150 155 160

Gly Gln Ala Ser Pro Ser Arg Ile Asp Gly Thr His Gln Thr Leu Gln
165 170 175

Gly Ala Asp Leu Thr Val Ile Gly Ala Arg Asp Asp Leu Met Val Asn
180 185 190

Asn Ala Gly Leu Val Cys Gly Gly Val His Thr Ala Asn Ala Thr Val
195 200 205

Tyr Met Ile Asp Thr Val Leu Met Pro Pro Ala Gln
210 215 220

<210> SEQ ID NO 38
<211> LENGTH: 103
<212> TYPE: PRT
<213> ORGANISM: Mycobacterium bovis

<400> SEQUENCE: 38

```
Met Thr Glu Asn Leu Thr Val Gln Pro Glu Arg Leu Gly Val Leu Ala
1               5                   10                  15

Ser His His Asp Asn Ala Ala Val Asp Ala Ser Ser Gly Val Glu Ala
            20                  25                  30

Ala Ala Gly Leu Gly Glu Ser Val Ala Ile Thr His Gly Pro Tyr Cys
        35                  40                  45

Ser Gln Phe Asn Asp Thr Leu Asn Val Tyr Leu Thr Ala His Asn Ala
    50                  55                  60

Leu Gly Ser Ser Leu His Thr Ala Gly Val Asp Leu Ala Lys Ser Leu
65                  70                  75                  80

Arg Ile Ala Ala Lys Ile Tyr Ser Glu Ala Asp Glu Ala Trp Arg Lys
                85                  90                  95

Ala Ile Asp Gly Leu Phe Thr
            100
```

<210> SEQ ID NO 39
<211> LENGTH: 193
<212> TYPE: PRT
<213> ORGANISM: Mycobacterium bovis

<400> SEQUENCE: 39

```
Met Lys Val Lys Asn Thr Ile Ala Ala Thr Ser Phe Ala Ala Ala Gly
1               5                   10                  15

Leu Ala Ala Leu Ala Val Ala Val Ser Pro Pro Ala Ala Ala Gly Asp
            20                  25                  30

Leu Val Gly Pro Gly Cys Ala Glu Tyr Ala Ala Ala Asn Pro Thr Gly
        35                  40                  45

Pro Ala Ser Val Gln Gly Met Ser Gln Asp Pro Val Ala Val Ala Ala
    50                  55                  60

Ser Asn Asn Pro Glu Leu Thr Thr Leu Thr Ala Ala Leu Ser Gly Gln
65                  70                  75                  80

Leu Asn Pro Gln Val Asn Leu Val Asp Thr Leu Asn Ser Gly Gln Tyr
                85                  90                  95

Thr Val Phe Ala Pro Thr Asn Ala Ala Phe Ser Lys Leu Pro Ala Ser
            100                 105                 110

Thr Ile Asp Glu Leu Lys Thr Asn Ser Ser Leu Leu Thr Ser Ile Leu
        115                 120                 125

Thr Tyr His Val Val Ala Gly Gln Thr Ser Pro Ala Asn Val Val Gly
    130                 135                 140

Thr Arg Gln Thr Leu Gln Gly Ala Ser Val Thr Val Thr Gly Gln Gly
145                 150                 155                 160

Asn Ser Leu Lys Val Gly Asn Ala Asp Val Val Cys Gly Gly Val Ser
                165                 170                 175

Thr Ala Asn Ala Thr Val Tyr Met Ile Asp Ser Val Leu Met Pro Pro
            180                 185                 190

Ala
```

DIAGNOSTIC REAGENTS

FIELD OF INVENTION

The present invention relates to reagents for use in a skin test for detection of mycobacterium infections, particularly *Mycobacterium tuberculosis* and *M. bovis*, in mammals such as cattle.

BACKGROUND

*M. tuberculosis* and *M. bovis* are important pathogens of man and animals. *M. tuberculosis* is thought to infect up to a third of the world's human population, remaining undetected during a latent phase of infection and reactivating to cause 10 million cases of tuberculosis and other diseases per year, resulting in 2 million deaths (Corbett et al. (2003) Arch. Intern. Med. vol. 163 pp 1009-1021). *M. bovis*, which has more than 99.9% sequence identity with *M. tuberculosis*, is the causative agent of bovine tuberculosis (BTB) and also causes disease in human. BTB represents a significant economic burden to the agricultural industries of various countries including the United Kingdom (Krebs (1997) "Bovine Tuberculosis in Cattle & Badgers" HMSO, London, United Kingdom).

The primary diagnostic test used in the control and surveillance of bovine TB is the tuberculin skin-test, a test that has remained in the forefront of TB diagnosis in both man and cattle for over 100 years. The development of the test arose following the preparation of the first 'tuberculin' by Robert Koch in 1890. Whilst Koch's tuberculin failed to live up to its initial claims of having curative properties, its diagnostic potential was quickly realised. The most common formats of the test used in cattle are the caudal fold test (CFT), the single intradermal cervical tuberculin test (SIT) and the single intradermal comparative cervical tuberculin (SICCT) test (Monaghan et al. (1994) Vet. Microbiol. vol. 40 pp 111-24). These test formats use a purified protein derivative (PPD) tuberculin prepared from a culture of *M. bovis* (PPD-B) as the primary diagnostic antigen. Additionally, the SICCT test includes the use of a *M. avium* derived PPD (PPD-A) to provide a measure of environmental sensitisation. It is the most specific of the tests (Plum (1931) Cornell Vet. vol. 21 pp 68-76; Stenius (1938) Veterinary Record vol. 50 pp 633-7) and is, therefore, the adopted test format in the UK.

In addition to skin tests, blood-based diagnostic assays that measure antigen-induced lymphokine production such as the interferon gamma (IFN-γ) test are also under consideration. The cytokine IFN-γ appears to be critical in the development of immunity to *M. tuberculosis*. For example, mice with a disrupted IFN-γ gene and also humans with a mutated IFN-γ receptor are highly susceptible to mycobacterial infections. However, specificity constraints are associated with the use of PPD in such assays. These arise due to the crude mixture of *M. bovis* proteins that PPD contains, many of which are cross-reactive with the BCG vaccine strain and environmental mycobacterial species such as *M. avium* and *M. intracellulare.*

Bovine TB is a significant and ongoing problem in the UK. Cattle vaccination has been identified as one of the most promising long term UK control strategies (Krebs (1997) "Bovine Tuberculosis in Cattle & Badgers" HMSO) and the development of an efficacious vaccine continues to be a research priority. Currently, promising vaccines against bovine TB are based on heterologous prime-boost combinations that include the live attenuated *M. bovis* vaccine strain Bacille Calmette-Guerin (BCG) as one of their components (Hogarth et al. (2006) J. Pharm. Pharmacol. vol. 58 pp 749-57). However, as in humans, vaccination of cattle with BCG compromises the specificity of the tuberculin skin-test since PPD contains cross reactive antigens shared by both pathogenic and vaccine strains (Berggren (1981) Br. Vet. J. vol. 137 pp 88-94; Buddle et al. (1999) Clin. Diagn. Lab. Immunol. vol. 6 pp 1-5; Waddington & Ellwood (1972) Br. Vet. J. vol. 128 pp 541-52). Therefore, the development of diagnostic tests that can differentiate vaccinated from infected animals, so-called DIVA tests, are an essential pre-requisite to allow the inclusion of BCG-based vaccination as part of bovine TB control strategies.

Previous studies have demonstrated that diagnostic reagents which distinguish between vaccinated and infected cattle can be developed using specific, defined antigens that are present in virulent *M. bovis* but absent from the BCG. Genetic analysis of BCG has revealed that several large genomic regions have been deleted during attenuation and subsequent prolonged propagation in culture. These regions have been characterised and antigens from one of these regions, RD1, have been studied extensively in several species including humans and cattle. For example, it has been demonstrated that protein or polypeptide cocktails composed of two RD1 region antigens, ESAT-6 and CFP-10, can be used to distinguish between *M. bovis* infected and BCG-vaccinated cattle.

The practical application of such DIVA reagents have so far been largely realised through their use in blood-based interferon-.gamma. (IFN-.gamma.) release assays (IGRAs). For example, WO2009/060184 disclosed several polypeptides including epitopes from Rv3615c which were found to be useful to detect *M. bovis* infection, using such an assay. This polypeptide has also been confirmed as useful to detect *M. tuberculosis* infection in humans (Millington et al. (2011) Proc. Natl. Acad. Sci. USA vol. 108 pp 5730-5735). Rv3615c is referred to herein using the *M. tuberculosis* genome annotation. In the *M. bovis* genome, it is annotated as Mb3645c.

Given the high level of familiarity and wide-spread application of the tuberculin skin-test by veterinarians and clinicians, a DIVA skin-test format would provide a valuable additional test platform. This might especially be the case where the logistics of access to laboratory-based resources is problematic. It is also notable that, in recent years, there has also been renewed interest in a skin-test based DIVA test for human TB with several reports demonstrating the skin-test potential of ESAT-6 (Aggerbeck & Madsen (2006) Tuberculosis (Edinb.) vol. 86 pp 363-73; Arend et al. (2000) J. Infect. Dis. vol. 181 pp 1850-4; Wu et al. (2008) Clin. Exp. Immunol. vol. 152 pp 81-7). However, Whelan et al. (Infect. Immun. (2003) col. 71 pp 6420-6425) found that ESAT-6 was not effective on its own as a skin test reagent in cattle assessed using measurement of skin induration at the injection site. The addition of a synthetic bacterial lipopeptide adjuvant was required before ESAT-6 proved useful in cattle. It is preferable to avoid the use of adjuvants in a skin test reagent, since repeat skin test injections (as is required to monitor the health of, for example, a herd of dairy cattle) may lead to the sensitisation of non-tuberculosis infected animals, so that the skin test would cease to be useful to differentiate between infected animals and uninfected but vaccinated animals.

The present invention accordingly addresses the problem of providing discriminatory diagnostic reagents for the detection of mycobacterial infections using a DIVA skin-test format.

SUMMARY OF INVENTION

According to a first aspect of the invention, there is provided a skin test diagnostic reagent comprising at least one CFP-10 epitope polypeptide, at least one ESAT-6 epitope polypeptide and at least one Rv3615c epitope polypeptide, characterised in that the diagnostic reagent is capable of eliciting a positive result when administered in a skin test to an animal infected with *Mycobacterium bovis* or *Mycobacterium tuberculosis*. In one embodiment, the reagent does not comprise an adjuvant, i.e., a reagent that assists in propagating an immune response to enhance the effect of the diagnostic reagent but which does not itself induce an immune response. An example is a bacterial lipopeptide and the skilled person is readily able to determine the identity of a suitable adjuvant in a given context.

This invention arises from the inventors' discovery that this particular combination of polypeptides (CFP-10, ESAT-6 and Rv3615c or fragments thereof) provides unexpectedly good results when used in a skin test for bovine tuberculosis. CFP-10 has not previously been assessed for use in a skin test. Furthermore, the inventors have found that ESAT-6 is only useful in a skin test in cattle when used in conjunction with an adjuvant. The inventors have now surprisingly found that using both proteins in combination with an Rv3615c epitope polypeptide elicited more accurate and sensitive results than when any of the three proteins is used alone. Advantageously, this combination of proteins enables the use of a skin test capable of distinguishing between *M. bovis* and/or *M. tuberculosis* infected animals and animals which have been vaccinated against infection by *M. bovis* and/or *M. tuberculosis*, for example, with a BCG vaccine.

The animal may be a mammal such as a cow, a badger or a human being.

The term "epitope polypeptide", as used throughout this specification, indicates a polypeptide which includes one or more (or all) epitopes of the relevant protein. Therefore, for example, a CFP-10 epitope polypeptide indicates the full length CFP-10 protein or a fragment thereof which includes at least one CFP-10 epitope. The term "epitope" refers to the amino acids (typically a group of around 5 or more amino acids) within a polypeptide sequence which are essential in the generation of an immune response and which can, therefore, be used in a diagnostic test. The immune response may be an antibody mediated immune response, but may also be a non-antibody mediated immune response, for example, an immune response which can be detected by means of a cell-mediated immunity (CMI) assay. Therefore, the epitope may be one which is recognisable by a T cell, for example by binding of a T cell receptor to the epitope.

The epitope may comprise amino acids occurring consecutively in the protein or fragment, or the amino acids forming the epitope may be spaced apart from one another in the protein or fragment. In the latter case, the nature of the amino acids between the amino acids forming the epitope may not be crucial to the activity and may be varied, provided that the tertiary structure of the epitope is maintained, for example so that an immune response such as a cell-mediated immune response can occur in response to the presence of the epitope. Determination of the amino acids which form an epitope or part of an epitope can be undertaken using routine methods. For example, one of a series of small mutations such as point mutations may be made to a polypeptide and the mutated polypeptide assayed to determine whether the immunogenic or diagnostic activity has been retained. Where it has, then the variant retains the epitope. If activity has been lost, then the mutation has disrupted the epitope and so must be reversed.

Whether or not a particular fragment includes an epitope is readily determined by the skilled person, for example, by exposing the fragment to an antibody and determining whether the antibody binds to the fragment, or by use of a CMI assay as described above.

The skin test referred to herein may be any of a CFT, SIT or SICCT test, as described in the Office International des Epizooties (OIE) Manual of Diagnostic Tests and Vaccines for Terrestrial Animals (ISBN-10:92-9044-718-4). The manual provides information, definitions and guidelines on positive test criteria. Therefore, when the diagnostic reagent according to the invention elicits a positive result when administered in a skin test such as one of those mentioned above, this is determined, for example, by detection of an increased thickness and/or induration of skin at the site at which the diagnostic reagent has been injected, using callipers, for example. The skin thickness may ideally be determined, for example, prior to injection (to provide a starting thickness for comparison after injection) and at one or more of, for example, about 24, 36, 48, 72, 96 or about 120 hours after injection of the diagnostic reagent. Determining skin thickness at about 72 hours after injection is typical. Thickness may be determined at any time period after injection, provided that, when results from different tests are compared, they are compared after substantially the same time period after injection (e.g., between 1 and 10 hours before or after one of the time points mentioned above such as the 72 hour time point, for example, between 3 and 7 hours before or after or about 5 hours before or after).

The diagnostic reagent of the invention may comprise one or more of the three polypeptides having amino acid sequences SEQ ID NOs:35, 36 and 38, i.e., full length CFP-10, ESAT-6 and Rv3615c, respectively. In one embodiment, the diagnostic reagent comprises all of SEQ ID NOs:35, 36 and 38.

Alternatively or additionally, the diagnostic reagent may comprise at least 1, 2, 3, 4, 5, 6, 7, 8, 9 or 10 polypeptides each having one of amino acid sequences SEQ ID NOs:1-10. These sequences are polypeptides which are overlapping fragments of CFP-10 which are CFP-10 epitope polypeptides, i.e., each of them contains at least one CFP-10 epitope.

Alternatively or additionally, the diagnostic reagent may comprise at least 1, 2, 3, 4, 5, 6, 7, 8, 9, 10 or 11 polypeptides each having one of amino acid sequences SEQ ID NOs:11-21. These sequences are polypeptides which are overlapping fragments of ESAT-6 which are ESAT-6 epitope polypeptides, i.e., each of them contains at least one ESAT-6 epitope.

Alternatively or additionally, the diagnostic reagent may comprise at least 1, 2, 3, 4, 5, 6, 7, 8, 9, 10, 11 or 12 polypeptides each having one of amino acid sequences SEQ ID NOs: 23-34. These sequences are polypeptides which are overlapping fragments of Rv3615c which are Rv3615c epitope polypeptides, i.e., each of them contains at least one Rv3615c epitope. For example, the diagnostic reagent may comprise the polypeptides having one or more of amino acid sequences SEQ ID NOs:29, 30, 31, 32, 33 and 34, for example, one or more of amino acid sequences SEQ ID NOs:31, 32 and 34, or one or both of amino acid sequence SEQ ID NOs:33 and 34, or may comprise the polypeptides having amino acid sequence SEQ ID NOs:23-33, or may comprise the polypeptides having amino acid sequence SEQ ID NOs:23-34. In any of these embodiments, the diagnostic reagent may further comprise at least one of the polypeptides having amino acid sequences SEQ ID NOs:22 or 37.

The diagnostic reagent may further comprise at least one MPB83 epitope polypeptide, for example a polypeptide having amino acid sequence SEQ ID NO:37. This sequence is the amino acid sequence of MPB83 (identified in WO97/08322). The inventors surprisingly found that including this protein elicited more accurate and sensitive results when combined with CFP-10 and ESAT-6 proteins, even though MPB83 protein alone has poor IFN-γ inducing capacity, in comparison to CFP-10 and ESAT-6. Alternatively or additionally, the diagnostic reagent may comprise at least one polypeptide having amino acid sequence SEQ ID NO:22. This sequence is a MPB83 epitope polypeptide, i.e., it contains at least one MPB83 epitope.

The diagnostic reagent may further comprise at least one MPB70 epitope polypeptide, for example a polypeptide having amino acid sequence SEQ ID NO:39. This sequence is the amino acid sequence of MPB70.

The diagnostic reagent may comprise any combination of one or more of the polypeptides having amino acid sequences SEQ ID NOs:1-39, provided that at least one CFP-10 epitope polypeptide, at least one ESAT-6 epitope polypeptide and at least one Rv3615c epitope polypeptide is included. The polypeptides may be included in the diagnostic reagent in individual form, or in the form of one or more fusion proteins. For example, a fusion protein comprising SEQ ID NOs:35, 36 and 38 may form the diagnostic reagent according to the invention.

In one embodiment, the diagnostic reagent comprises the polypeptides having amino acid sequences SEQ ID NOs:1-22, 31, 32 and 34, or the polypeptides having amino acid sequences SEQ ID NOs:1-22, 30, 32 and 33, or the polypeptides having amino acid sequences SEQ ID NOs:1-22, 32, 33 and 34, or comprises the polypeptides having amino acid sequences SEQ ID NOs:1-22, 33 and 34. In an alternative embodiment, the diagnostic reagent comprises the polypeptides having amino acid sequences SEQ ID NOs:1-33, or comprises the polypeptides having amino acid sequences SEQ ID NOs:1-34.

The diagnostic reagent may be for use in a method of detecting *Mycobacterium bovis* or *Mycobacterium tuberculosis* infection in an animal using a skin test.

The diagnostic reagent may be in the form of a sterile injectable preparation which may be an aqueous or an oleaginous suspension, or a suspension in a non-toxic parenterally-acceptable diluent or solvent. The aqueous suspension may be prepared in, for example, mannitol, water, Ringer's solution or isotonic sodium chloride solution. Alternatively, it may be prepared in phosphate buffered saline solution. The oleaginous suspension may be prepared in a synthetic monoglyceride, a synthetic diglyceride, a fatty acid or a natural pharmaceutically-acceptable oil. The fatty acid may be an oleic acid or an oleic acid glyceride derivative. The natural pharmaceutically-acceptable oil may be an olive oil, a castor oil, or a polyoxyethylated olive oil or castor oil. The oleaginous suspension may contain a long-chain alcohol diluent or dispersant, for example, Ph. Helv.

In an embodiment, the diagnostic reagent is able (and, therefore, allows a user) to differentiate between an *M. bovis*-and/or *M. tuberculosis*-infected animal and an animal vaccinated against *M. bovis* or *M. tuberculosis* (for example, an animal vaccinated with the live attenuated vaccine BCG).

According to a second aspect of the invention, there is provided a method of detecting *Mycobacterium bovis* or *Mycobacterium tuberculosis* infection in an animal comprising conducting a skin test on the animal using at least one diagnostic reagent according to the first aspect of the invention. The animal may be a mammal, for example a cow, a badger or a human being. The method may further comprise a step of correlating a positive skin test result with infection of an animal with *Mycobacterium bovis* or *Mycobacterium tuberculosis* and a step of diagnosing said animal as being infected by *Mycobacterium bovis* or *Mycobacterium tuberculosis*.

"Using" and "use" of polypeptides and diagnostic reagents in the skin test included in method according to this aspect of the invention typically involves intradermal injection of the polypeptide(s) and/or diagnostic reagent into the animal. A skin test for use in the invention may be conducted as described in OIE Manual of Diagnostic Tests and Vaccines for Terrestrial Animals, as mentioned above.

According to a third aspect of the invention, there is provided a diagnostic kit comprising a diagnostic reagent according to the first aspect of the invention. The diagnostic kit may be for use in the method of the second aspect of the invention. The diagnostic reagent may be in liquid form, as outlined above, or may be in solid (for example, lyophilised) form. It may be included in the kit in the form of at least one aliquot of 0.05-0.15 ml containing 1-15 μg of each polypeptide contained in the diagnostic reagent. For example, the kit may comprise aliquots of about 0.05 ml, about 0.06 ml, about 0.07 ml, about 0.08 ml, about 0.09 ml, about 0.1 ml, about 0.11 ml, about 0.12 ml, about 0.13 ml, about 0.14 ml or about 0.15 ml, containing 1-15 μg, for example, 3-12 μg or 5-10 μg of each epitope polypeptide, for example, about 5 μg, about 6 μg, about 7 μg, about 8 μg, about 9 μg or about 10 μg of each epitope polypeptide. Each aliquot may be contained in a disposable injection device. The kit may further comprise at least one sample of PPD. The diagnostic reagent may be able to detect a *M. bovis* or *M. tuberculosis* infection in a mammal and may be able to differentiate between an *M. bovis*- or *M. tuberculosis*-infected mammal and a mammal vaccinated against infection by *M. bovis* or *M. tuberculosis*.

The present invention also encompasses diagnostic reagents comprising variants of the epitope polypeptides and methods utilising these variant polypeptides. As used herein, a "variant" means a polypeptide in which the amino acid sequence differs from the base sequence from which it is derived in that one or more amino acids within the sequence are substituted for other amino acids. The variant is a functional variant, in that the functional characteristics of the polypeptide from which the variant is derived are maintained. For example, a similar immune response is elicited by exposure of an animal, or a sample from an animal, to the variant polypeptide as to the non-variant. In particular, any amino acid substitutions, additions or deletions must not alter or significantly alter the tertiary structure of one or more epitopes contained within the polypeptide from which the variant is derived. The skilled person is readily able to determine appropriate functional variants and to determine the tertiary structure of an epitope and any alterations thereof, without the application of inventive skill.

Amino acid substitutions may be regarded as "conservative" where an amino acid is replaced with a different amino acid with broadly similar properties. Non-conservative substitutions are where amino acids are replaced with amino acids of a different type.

By "conservative substitution" is meant the substitution of an amino acid by another amino acid of the same class, in which the classes are defined as follows:

| Class | Amino acid examples |
|---|---|
| Nonpolar: | Ala, Val, Leu, Ile, Pro, Met, Phe, Trp |
| Uncharged polar: | Gly, Ser, Thr, Cys, Tyr, Asn, Gln |
| Acidic: | Asp, Glu |
| Basic: | Lys, Arg, His. |

As is well known to those skilled in the art, altering the primary structure of a polypeptide by a conservative substitution may not significantly alter the activity of that polypeptide because the side-chain of the amino acid which is inserted into the sequence may be able to form similar bonds and contacts as the side chain of the amino acid which has been substituted out. This is so even when the substitution is in a region which is critical in determining the polypeptide's conformation.

As mentioned above, non-conservative substitutions are possible provided that these do not disrupt the tertiary structure of an epitope within the polypeptide, for example, which do not interrupt the immunogenicity (for example, the antigenicity) of the polypeptide.

Broadly speaking, fewer non-conservative substitutions will be possible without altering the biological activity of the polypeptide. Suitably, variants may be at least 50% identical, 60% identical, for example at least 75% identical, such as at least 90% identical to the base sequence.

Sequence identity between amino acid sequences can be determined by comparing an alignment of the sequences. When an equivalent position in the compared sequences is occupied by the same amino acid, then the molecules are identical at that position. Scoring an alignment as a percentage of identity is a function of the number of identical amino acids at positions shared by the compared sequences. When comparing sequences, optimal alignments may require gaps to be introduced into one or more of the sequences, to take into consideration possible insertions and deletions in the sequences. Sequence comparison methods may employ gap penalties so that, for the same number of identical molecules in sequences being compared, a sequence alignment with as few gaps as possible, reflecting higher relatedness between the two compared sequences, will achieve a higher score than one with many gaps. Calculation of maximum percent identity involves the production of an optimal alignment, taking into consideration gap penalties. The percentage sequence identity may be determined using the BLASTP software using default parameter settings.

According to a fourth aspect of the invention there is provided a diagnostic reagent according to a first aspect of the invention for use in a method for diagnosing infection of an animal by *Mycobacterium bovis* or *Mycobacterium tuberculosis*, the method comprising the steps of conducting a method according to the second aspect of the invention on the animal and correlating a positive skin test result with infection of the animal by *Mycobacterium bovis* or *Mycobacterium tuberculosis*, hence diagnosing the animal as being infected with *Mycobacterium bovis* or *Mycobacterium tuberculosis*.

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Any features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

BRIEF DESCRIPTION OF FIGURES

Particular non-limiting examples of the present invention will now be described with reference to the following Figures, in which.

EXAMPLES

Materials and Methods

Animals

Figure 1:
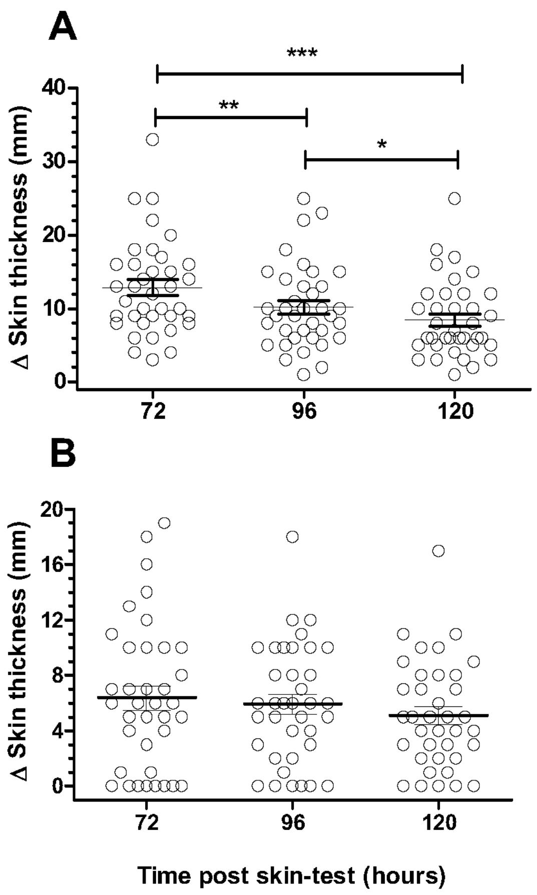
FIG. 1 shows protein-cocktail induced skin-test responses in cattle, with A showing comparative SICCT PPD responses [(PPD-B)-(PPD-A)] and B showing responses induced by a cocktail of 10 μg each of the proteins ESAT-6, CFP-10, MPB70.

To investigate the skin-test performance of defined antigens in cattle naturally exposed to *M. bovis*, SICCT reactor cattle were recruited from UK farms with a confirmed history of bovine TB (convenience sampling dependent on availability). Animals were identified during routine surveillance operations where their SICCT response [(PPD-B)-(PPD-A)]> 2 mm and housed in secure segregated bio-containment facilities at the Veterinary Laboratories Agency (VLA). A total of 62 reactors were used in the study which included 21 male and 41 female cattle of 7 different breeds, including dairy and beef stock. Age at time of study skin-test investigations ranged from 9 months to 11 years, with a median age of 21 months. All reactors underwent detailed post mortem examination to assess for presence of *M. bovis* infection, in accordance with previously described procedures (Vordermeier et al. (2002) Infect. Immun. vol. 70 pp 3026-32). Visible lesions consistent with bovine TB and/or culture isolation of *M. bovis* were confirmed in 55 of these reactors.

For the specificity studies, Holstein-Friesian castrated male cattle (n=54) were sourced from UK TB-free farms and housed at VLA in separate accommodation from the reactors. A cohort of these calves (n=20) were neo-natally vaccinated with BCG to allow DIVA evaluation of reagents. A single dose of $1\times10^6$ CFU of BCG Danish (Staten Serum Institute, Sweden) was administered subcutaneously to each of these calves at 4-6 weeks of age. Where a second skin-test was performed in some cattle during the study, the second skin-test was performed no earlier than 62 days later. All cattle experiments were cleared by local ethical review and animal procedures under a license granted by the British Home Office.

Antigens

Bovine and avian PPDs were supplied by the VLA Tuberculin Production Unit. Histidine tagged recombinant proteins were expressed in *Escherichia coli* and purified by nickel affinity chromatography.

MPB70, MPB83, ESAT-6 and CFP-10 were supplied by Lionex Diagnostics and Therapeutics GmbH (Germany) and Rv3615c was produced at the Agri-Food and Biosciences Institute (Belfast, Northern Ireland). The Rv3615c synthetic protein fragment polypeptides (SEQ ID NOs:23-34) were synthesised by solid phase F-moc chemistry and supplied at a purity of >90% (Pepceuticals Ltd, UK). The identity of each polypeptide was confirmed by mass spectrometry. For ESAT-6 and CFP-10, 16mer protein fragment polypeptides with 8 amino acid overlaps of the complete protein sequences were used (21 polypeptides in total, having SEQ ID NOs:1-10 for CFP10 polypeptides and SEQ ID NOs:11-21 for ESAT-6 polypeptides).

For MPB83, a single 20mer protein fragment polypeptide (SEQ ID NO:22) that had previously been shown to encode a bovine T-cell epitope (p195-214) was used (Vordermeier et al. (1999) Clin. Diagn. Lab. Immunol. vol. 6 pp 675-82). Similarly, for Rv3615c, in initial experiments three bovine T-cell epitope-encoding 20mer protein fragment polypeptides were used (p65-84 (SEQ ID NO:31), p73-92 (SEQ ID NO:32) and p84-103 (SEQ ID NO:34)) (Sidders et al. (2008) Infect. Immun. vol. 76 pp 3932-9). In subsequent experiments, a cocktail of SEQ ID NOs:23-33 was used.

All proteins and polypeptides and cocktails were prepared in phosphate buffered saline (PBS), pH7.4, for use in the following experiments.

Skin Test Procedures

The disclosing SICCT field-test was performed and interpreted according to OIE Manual of Diagnostic Tests and Vaccines for Terrestrial Animals. For the evaluation of defined antigen combinations at VLA, up to 8 intradermal injection sites were used on each animal, 4 on each side of the neck. PPD-B and PPD-A (2500 IU) were always included at each test and all antigens were administered in a 0.1 ml volume. Defined antigens were tested at a concentration 10 μg whether used individually or as a component of a cocktail unless otherwise stated. Skin-induration at administration sites was measured using callipers by the same operator for all experiments. Measurements were recorded prior to and at 72 hours post skin-test and, additionally, at 96 and 120 hours for some experiments. Results are expressed as the difference in skin thickness (mm) between the pre and post skin-test readings.

IFN-γ Whole Blood ELISA

Heparinised whole blood cultures were stimulated with either PPD-A (10 μg/ml), PPD-B (10 μg/ml), recombinant protein antigens (5 μg/ml), protein cocktail (5 μg/ml per constituent), staphylococcal enterotoxin B (SEB) (1 μg/ml Sigma-Aldrich, UK) or no-antigen control. Cultures were set up within 8 hours of blood collection and cultured at 37° C./5% $CO_2$. Antigen stimulated IFN-γ was measured in 24 hour whole blood culture supernatants using the commercially available BOVIGAM® ELISA (Prionics AG, Switzerland). Results are expressed as the background-corrected optical density measured at 450 nm ($OD_{450nm}$).

Statistical Analysis

Differences in response magnitude between different antigen combinations were compared by repeated measures ANOVA, with application of Bonferroni's Multiple Comparison post-analysis test. Differences between antigen responder frequencies were analysed using the Fisher Exact Test. These statistical analyses and Receiver Operator Curve (ROC) analysis were performed using the Prism 5 software program (Graphpad Inc, USA).

Results

A Defined Protein Cocktail of MPB70, MPB83, ESAT-6 and CFP-10 Induces Skin-Test Responses in Naturally Infected Cattle To assess the potential of defined antigens as diagnostic skin-test reagents, the inventors initially formulated a cocktail comprising the purified recombinant *M. bovis/M. tuberculosis* protein antigens ESAT-6, CFP-10, MPB70 and MPB83. MPB70 and MPB83 were included in the cocktail since they had previous demonstrated DIVA skin-test potential in guinea model of *M. bovis* infection (Vordermeier et al. (1999) Clin. Diagn. Lab. Immunol. vol. 6 pp 675-82). In 37 SICCT positive cattle, the protein cocktail induce a response in 29/37 (78%) of these cattle at 72 hours post-test (FIG. 1). The increase in skin induration for each animal is represented by an open circle, the horizontal line provides the mean (±SEM) with results expressed as the difference in skin thickness (mm) between the pre and post skin-test readings. Statistical difference between responses was determined using by ANOVA (* $p<0.05$,  $p<0.01$, * $p<0.001$).

Skin reactions were additionally measured at 96 and 120 hours since it has previously been reported that the development of bovine skin-test responses to ESAT-6 continued to increase after 72 hours (Pollock et al. (2003) J. Clin. Microbiol. vol. 41 pp 1856-60). In comparison with the 72 hour reactions, the SICCT responses were significantly reduced at 96 and 120 hours post-test (FIG. 1). The magnitude of protein cocktail-induced reactions was comparable at each time point.

Figure 2:
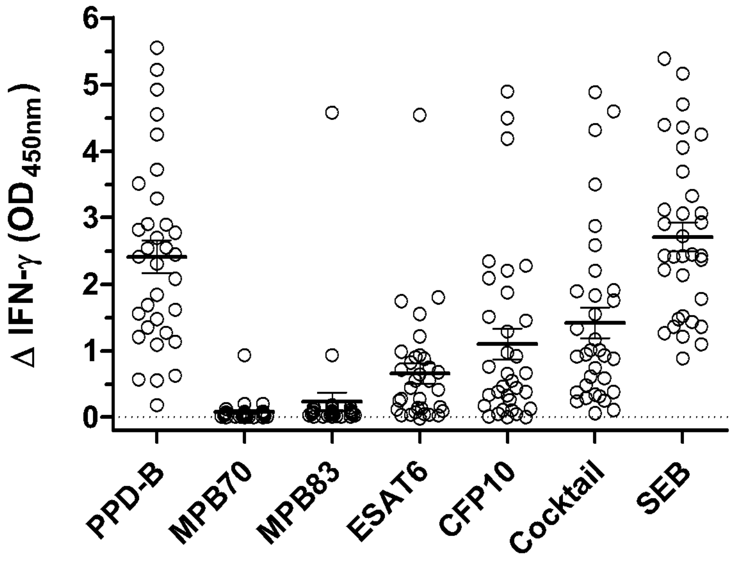
FIG. 2 shows the in vitro capacity of antigens to induce IFN-γ in blood from cattle naturally exposed to *M. bovis* (n=37), determined for the proteins ESAT-6, CFP-10, MPB70 and MPB83 either individually (5 μg/ml) or as a combined protein cocktail (5 μg/ml per constituent)

Measurement of antigen induced IFN-γ in whole blood cultures set up on the day of the skin-test demonstrated that ESAT-6 and CFP-10 were the most strongly recognised constituent antigens in the protein cocktail in vitro (FIG. 2). The in vitro capacity of antigens to induce IFN-γ in blood from cattle naturally exposed to *M. bovis* (n=37) was determined for ESAT-6, CFP-10, MPB70 and MPB83 either individually (5 μg/ml) or as a combined protein cocktail (5 μg/ml per constituent). Responses induced by PPD-B (10 μg/ml), SEB (1 μg/ml) or no-antigen control were also determined. The antigen induced IFN-γ response for each animal is represented by an open circle, the horizontal line provides the mean (±SEM) with results expressed as the background-corrected optical density measured at 450 nm ($OD_{450nm}$).

Figure 3:
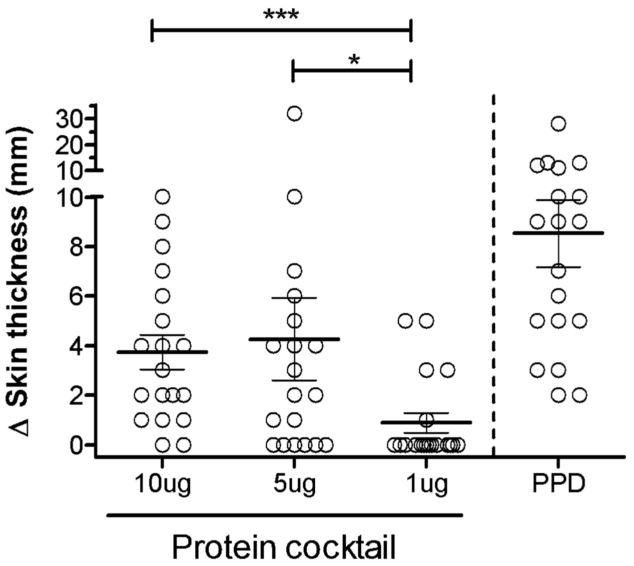
FIG. 3 shows skin-test dose titration protein-cocktail comprising ESAT-6, CFP-10, MPB70 and MPB83 proteins in cattle that were naturally exposed to *M. bovis* (n=19)

The protein cocktail was next tested at a titrated dose concentration of 10, 5 and 1 μg for each cocktail component. The respective responses in a cohort of 19 of the previously tested reactors are shown in FIG. 3. A skin-test dose titration was determined for the protein cocktail compromising ESAT-6, CFP-10, MPB70 and MPB83 in cattle that were naturally exposed to *M. bovis* (n=19). The protein cocktail was administered at a concentration of 10, 5 and 1 μg for each antigen component. Protein cocktail and SICCT [(PPD-B)-(PPD-A)] responses measured at 72 hours for each animal are represented by an open circle, the horizontal line provides the mean (±SEM) with results expressed as the difference in skin thickness (mm) between the pre and post skin-test readings. Statistical difference between responses induced by the protein cocktails was determined using by ANOVA (* p<0.05, *** p<0.001). Skin-test responses were comparable between the 10 and 5 μg dose but significantly reduced at the 1 μg dose demonstrating a dose response. For all further experiments, a skin-test concentration of 10 μg per defined antigen component was used.

Figure 4:
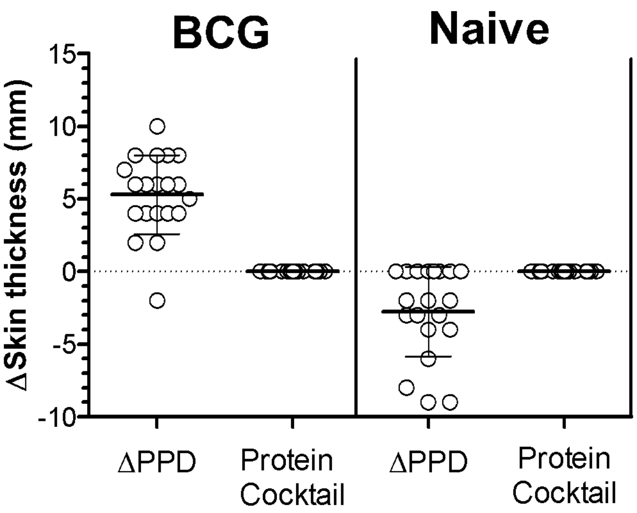
FIG. 4 shows skin-test specificity of the protein cocktail compromising ESAT-6, CFP-10, MPB70 and MPB83 proteins (10 μg for each component) and for the SICCT-test [(PPD-B)-(PPD-A)] in naïve TB-free (n=19) and BCG vaccinated (n=20) cattle.

The specificity of this protein cocktail was first determined in naïve cattle (n=20). The cocktail induced no measurable response in any of these animals when reactions were read at 72 hours (FIG. 4). Skin-test responses were measured for the protein cocktail compromising ESAT-6, CFP-10, MPB70 and MPB83 (10 μg for each component) and for the SICCT-test [(PPD-B)-(PPD-A)] in naïve TB-free (n=19) and BCG vaccinated (n=20) cattle. In FIG. 4, responses measured at 72 hours for each animal are represented by an open circle, the horizontal line provides the mean (±SEM) with results expressed as the difference in skin thickness (mm) between the pre and post skin-test readings. Whilst all SICCT responses were also negative, measurable PPD-A biased responses did indicate some sensitisation of these animals by environmental mycobacteria. Reactions were additionally measured at 96 and 120 hours. For all further experiments, reactions were only recorded at 72 hours post-test.

The DIVA potential of the protein cocktail was evaluated using 3-month old calves that had been neo-natally vaccinated with BCG at 4-6 weeks of age (n=20). In these calves, only one animal failed to induce a SICCT PPD-B biased skin-test, response confirming the strong tuberculin skin-test sensitisation of BCG vaccination (FIG. 4). In contrast, the defined protein cocktail did not induce a response in any of these vaccinates. Protein cocktail and SICCT responses measured in either the naturally infected or BCG vaccinated cattle were used to generate ROC curves to provide estimates of DIVA skin-test sensitivity and specificity. Table 1 summarises the sensitivity and specificity estimates for a SICCT cut-off of >2 mm and >4 mm since these represent operational 'severe' and 'standard' test cut-offs used in UK surveillance operations. Also shown are the performance figures for SICCT and protein cocktail test cut-offs that provide 100% DIVA specificity for the respective tests.

TABLE 1

DIVA sensitivity and specificity ROC estimates for SICCT and defined protein cocktail based skin-tests

| Diagnostic Antigen | Cut-off (mm) | Sensitivity[a] (%) | Specificity[b] (%) | Area under curve | 95% CI |
|---|---|---|---|---|---|
| SICCT (PPD B-A) | >2 | 100 | 15.0 | 0.899 | 0.817-0.981 |
| SICCT (PPD B-A) | >4 | 94.1 | 40.0 | 0.899 | 0.817-0.981 |
| SICCT (PPD B-A) | >10 | 55.9 | 100 | 0.899 | 0.817-0.981 |
| Protein cocktail[c] | >1 | 73.6 | 100 | 0.882 | 0.791-0.974 |

[a]Sensitivity determined using diseased confirmed SICCT 'reactor' naturally infected cattle (n = 34).
[b]Specificity determined using disease free cattle, BCG-vaccinated calves (n = 20).
[c]Protein cocktail comprising 10 μg each of ESAT-6 (SEQ ID NO: 36), CFP-10 (SEQ ID NO: 35), MPB70 (SEQ ID NO: 39) and MPB83 (SEQ ID NO: 37).

Optimisation of Defined Skin-Test Reagents Including the Use of Rv3615c and Synthetic Polypeptides In vitro assessment of the capacity of the constituent protein cocktail antigens to induce IFN-γ suggested the immunodominance of ESAT-6 and CFP-10 (FIG. 2). Therefore, the additive benefit of the inclusion of MPB70 and MPB83 to a cocktail already containing ESAT-6 and CFP-10 was investigated. In a group of 12 previously untested naturally infected cattle, all of which induced positive SICCT responses (data not shown), 6/12 cattle induced a response to the cocktail containing all 4 antigens (1-6 mm responses) whilst only 3 of these cattle responded to the cocktail containing only ESAT-6 and CFP-10 (2, 3 and 6 mm responses). Although the difference in responder frequency was not significant, the result did indicate an additive benefit of including MPB70 and/or MPB83 to the cocktail.

Figure 5:
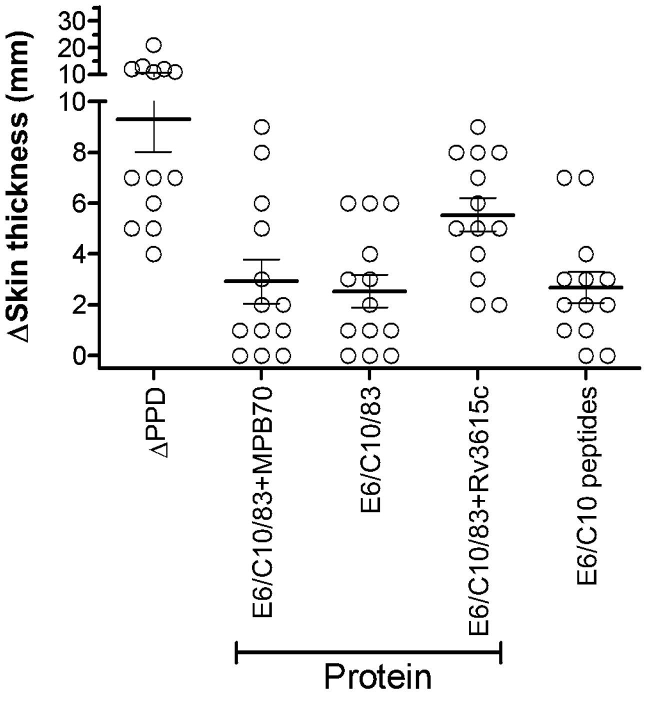
FIG. 5 shows skin-test responses induced by the SICCT-test [(PPD-B)-(PPD-A)] and a selection of protein and protein fragment polypeptide based antigen combinations, determined in cattle naturally exposed to *M. bovis* (n=13)

To determine if the inclusion of both MPB83 and MPB70 was required for optimal skin responses, protein cocktails formulated with and without MPB70 were tested in a further 13 naturally infected cattle. Additionally, this experiment was used as an opportunity to evaluate two novel defined antigen formulations. Firstly, a protein cocktail containing Rv3615c, a recently identified DIVA antigen which can identify *M. bovis* infected cattle that are unresponsive to ESAT-6 or CFP-10 (WO2009/060184 and Sidders et al. (2008) Infect. Immun. vol. 76 pp 3932-9). Secondly, a synthetic polypeptide cocktail comprising overlapping polypeptides of ESAT-6 and CFP-10. The results are shown in FIG. 5, in which responses measured at 72 hours for each animal are represented by an open circle, the horizontal line provides the mean (±SEM) with results expressed as the difference in skin thickness (mm) between the pre and post skin-test readings. Statistical difference between responses induced by the defined protein and polypeptide cocktails was determined using ANOVA (*** p<0.001).

The inclusion of MPB70 demonstrated no improvement in the responder frequency or magnitude of skin-reactions in these cattle, compared with those responses induced by the ESAT6, CFP-10 and MPB83 containing cocktail (FIG. 5). In contrast, the addition of Rv3615c increased responder frequency from 10/13 to 13/13 and also resulted in significantly stronger responses (FIG. 5). Protein combinations of ESAT-6 (E6), CFP-10 (C10), MPB70, MPB83 (83) and/or Rv3615c were all tested at 10 μg per constituent protein.

The ESAT-6 and CFP-10 (E6/C10) polypeptide cocktail included 21 polypeptides (SEQ ID NOs:1-21) at a concentration of 10 μg per polypeptide. As FIG. 5 shows, the ESAT-6/CFP-10 polypeptide cocktail induces responses in 11/13 cattle thus demonstrating their potential as skin-test antigens.

Figure 6:
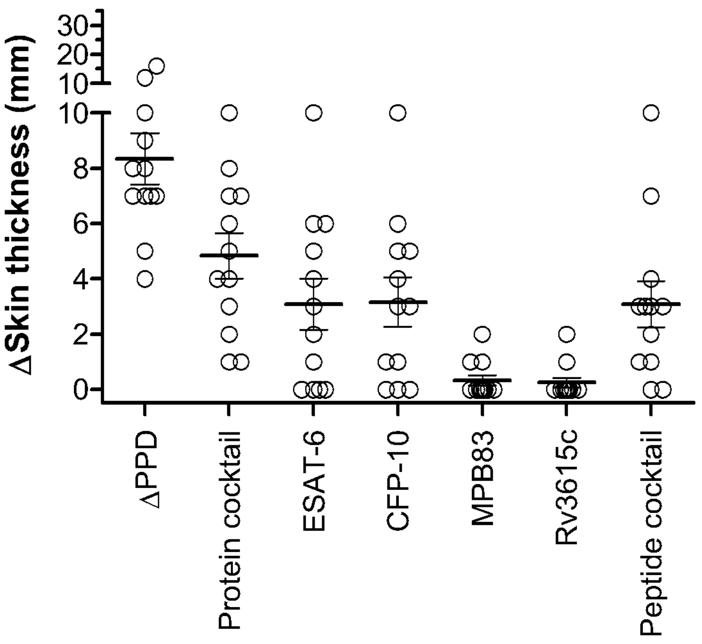
FIG. 6 shows skin-test responses induced by ESAT-6, CFP-10, MPB83 and Rv3615c proteins, determined either individually (10 μg) or in combination (10 μg per protein) in cattle naturally exposed to *M. bovis* (n=12)

The skin-test contribution of the individual antigens present in the protein cocktail comprising ESAT-6, CFP-10, MPB83 and Rv3615c was then investigated. The evaluation of synthetic polypeptide combinations was extended by testing a cocktail of polypeptides derived from CFP-10 (SEQ ID NOs:1-10), ESAT-6 (SEQ ID NOs:11-21), MPB83 (SEQ ID NO:22) and Rv3615c (SEQ ID NOs:31, 32 & 34). These reagents were tested in 12 reactor cattle that were selected from those used in the previous 2 experiments. All 9 animals that responded to any single antigen recognised CFP-10 (cut-off for positivity >1 mm) whilst 7, 3, and 2 responded to ESAT-6, MPB83 and Rv3615c respectively (FIG. 6). In FIG. 6, reactions measured at 72 hours for each animal are represented by an open circle, the horizontal line provides the mean (±SEM) with results expressed as the difference in skin thickness (mm) between the pre and post skin-test readings.

The combined protein cocktail provided maximal responder frequency and reaction size, including in 3 animals that failed to respond to any of the individual proteins. Encouragingly, the polypeptide cocktail induced responses in 10/12 of these cattle as shown in FIG. 6.

The specificity of the protein combination of ESAT-6, CFP-10, MPB83 and Rv3615c, as used above, was evaluated in 14 new naïve cattle and 19 of the BCG neo-natally vaccinated calves previously tested. The protein cocktail did not induce responses in any of these naïve or vaccinated cattle. Whilst 16/19 of the BCG vaccinates still demonstrated a PPD-B biased IFN-γ response at this time ([PPD-B]-[PPD-A]>0.1 $OD_{450nm}$, data not shown), it should be noted however that only 3/19 of the BCG vaccinates still elicited PPD-B biased skin reaction at this test, due to the extended period of nearly 12 months following neo-natal vaccination at this time (data not shown). Therefore, the use of the cocktail provides a more specific assay even after an extended period of up to 12 months post-vaccination.

The inventors also evaluated the skin-test performance of an ESAT-6/CFP-10 based diagnostic polypeptide cocktail that additionally includes 11 Rv3615c polypeptides disclosed in WO2009/060184 (SEQ ID NOs:23-33).

These 11 polypeptides provide fully overlapping coverage of residues 1-100 of the Rv3615c protein sequence. Therefore, the polypeptides in the cocktail were SEQ ID NOs:1-21 and 23-33. Skin-test responses were measured in SICCT-test positive (reactor) cattle (n=15). These animals were previously recruited from UK farms during routine TB surveillance operations. Skin reactions were measured 3 days following intradermal injection of antigens (100 μl injection volume). Each of the polypeptide cocktails contained an administered dose of 10 μg of each component polypeptide.

Figure 7:
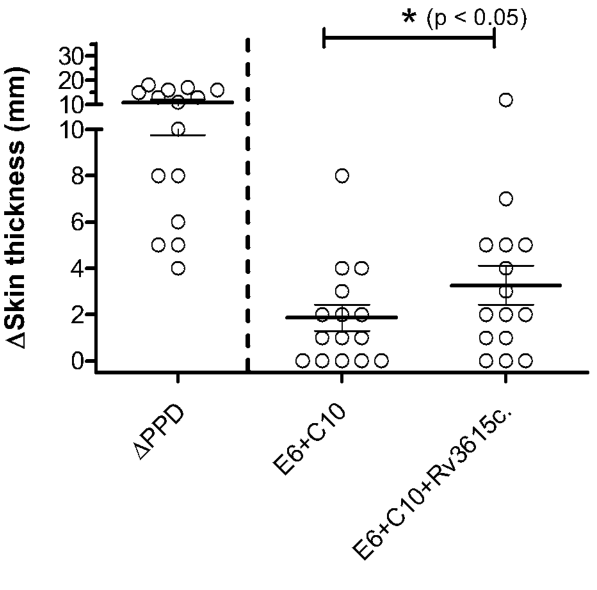
FIG. 7 shows the skin-test performance of an ESAT6/CFP10 based diagnostic protein fragment polypeptide cocktail that additionally includes 11 Rv3615c protein fragment polypeptides, measured in SICCT-test positive (reactor) cattle (n=15)

The increase in skin thickness 3 days following administration of antigens is shown in FIG. 7. All animals had SICCT positive skin-test. The addition of the 11 Rv3615c polypeptides to an ESAT-6/CFP-10 polypeptide-based cocktail resulted in significantly stronger skin-test responses compared with the cocktail containing polypeptides of ESAT6 and CFP10 alone (p=0.018, paired t-test).

Figure 8:
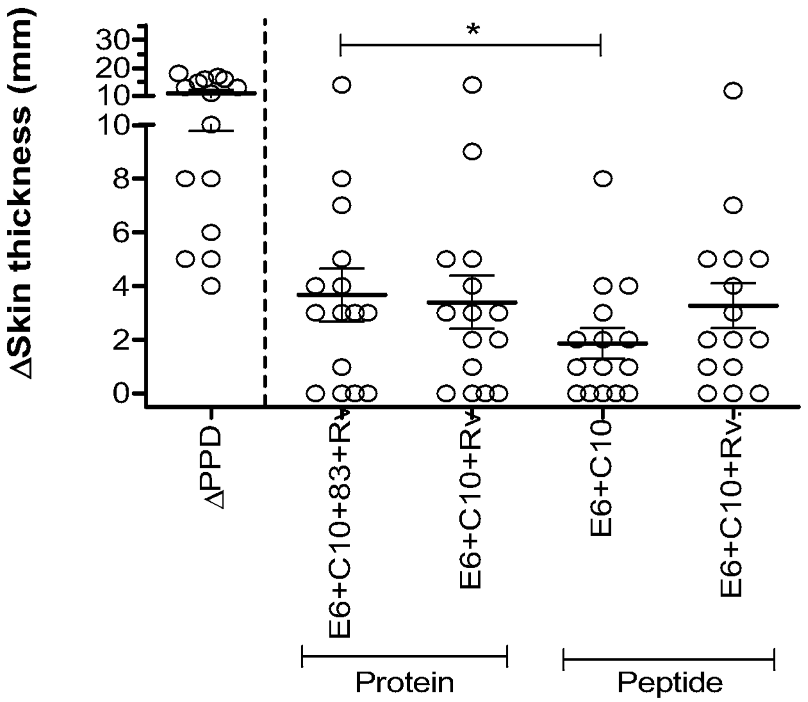
FIG. 8 shows the skin-test performance of an ESAT6/CFP10/MPB83/Rv3615c protein cocktail, an ESAT6/CFP10/Rv3615c protein cocktail, an ESAT6/CFP10 protein fragment polypeptide cocktail and an ESAT6/CFP10/Rv3615c protein fragment polypeptide cocktail, measured in SICCT-test positive (reactor) cattle (n=15).

Finally, the inventors determined that the optimal combination of epitope polypeptides (proteins or epitope polypeptide fragments) was ESAT-6, CFP-10 and Rv3615c. As can be seen in FIG. 8, no additional sensitivity of the skin test was achieved by the further inclusion of the protein MPB83.

Discussion

Previous investigations on the use of defined bovine skin-test reagents suggested that either immunomodulating reagents (Whelan et al. (2003) Infect. Immun. vol. 71 pp 6420-5) or high antigen doses (≥400 ug) (Pollock et al. (2003) J. Clin. Microbiol. vol. 41 pp 1856-60) might be required to provide sensitive skin-responses. It is therefore surprising that the current work demonstrated antigen specific skin-reactions in 78% of SICCT reactor cattle when using a protein-antigen combination of ESAT-6, CFP-10, MPB70 and MPB83, using an administered concentration of 10 μg per protein Importantly, this is a dose considered to be realistic for practical field applications. Furthermore, this skin-test cocktail was highly specific, eliciting no response in either naïve or BCG vaccinated calves. This is the first time that the DIVA potential of defined skin-test antigens has been demonstrated in BCG vaccinated/*M. bovis* infected cattle.

Assessment of the in vitro recognition of the individual antigens in the initial protein cocktail showed that MPB70 and MPB83 had poor IFN-γ inducing capacity in comparison with ESAT-6 and CFP-10. Therefore, despite their sub-dominant in vitro immunogenicity in cattle, it is surprising that their inclusion in the skin-test cocktail increased the skin-test responder frequency compared with using only ESAT-6 and CFP-10. In mice, it has been shown that during a DTH (delayed-type hypersensitivity) response, there must first be an early initiation phase which is required to recruit antigen specific T-cells which then propagate the classical late phase inflammatory response (van Loveren et al. (1983) J. Exp. Med. vol. 157 pp 1604-17). Furthermore, the antigens that induce the initiation and effector stages can be different (Ptak et al. (1986) J. Immunol. vol. 136 pp 1564-70). Therefore, without being bound by theory, it is possible that sub-dominant effector T-cell antigens such as MPB70 and MPB83 might still have a role in promoting reaction-initiation, thereby helping to elicit a better response to dominant effector antigens such as ESAT-6 and CFP-10.

Further optimisation of the skin-test protein cocktail demonstrated that the inclusion of MPB70 had no additional benefit over the use of MPB83. However, the addition of Rv3615c to a protein cocktail containing ESAT-6, CFP-10 and MPB83 did result in a significant improvement in skin-test responses and proved to be the most optimal antigen combination tested. The diagnostic potential of Rv3615c has only recently been identified, having been found to be recognised by infected cattle which did not respond to either ESAT-6 or CFP-10 (WO2009/060184 and Sidders et al. (2008) Infect. Immun. vol. 76 pp 3932-9). The present demonstration that it can also contribute to improved skin-test responses without compromising specificity further confirms its diagnostic importance. Furthermore, the inventors have shown that the advantages described herein are obtained using a combination of ESAT-6, CFP-10 and Rv3615c, with inclusion of MPB83 not being necessary for optimal skin test sensitivity when all three of the proteins (or epitope polypeptide fragments) are included.

An important practical advantage of synthetic polypeptides compared to recombinant proteins as diagnostic antigens is that, being chemically synthesised, quality control is more easily standardised. The practical application of synthetic polypeptides as bovine TB DIVA reagents using IFN-γ based blood assays (Vordermeier et al. (2001) Clin. Diagn. Lab. Immunol. vol. 8 pp 571-8) has previously been demonstrated and, similarly, they have also been applied for human TB diagnosis (Arend et al. (2000) J. Infect. Dis. vol. 181 pp 1850-4; Lalvani et al. (2001) J. Infect. Dis. vol. 183 pp 469-77). However, this is the first report demonstrating the potential of these protein fragment polypeptides as TB skin-test antigens in cattle. This data provides a basis for future optimisation and improvement of a polypeptide based skin-test.

In considering why the results of previous ESAT-6 based cattle skin-test studies looked less promising than the current data (Pollock et al. (2003) J. Clin. Microbiol. vol. 41 pp 1856-60; Whelan et al. (2003) Infect. Immun. vol 71 pp 6420-5), one explanation is likely to be the inclusion of CFP-10, which has not previously been evaluated as a bovine skin-test antigen. Notably, skin-test responses induced by the individual protein antigens showed CFP-10 to be the most potent defined antigen. Furthermore, the use of antigen combinations demonstrated clear sensitivity benefits in the current study and will also have contributed to the improved responses compared with the previous use of ESAT-6 alone (Pollock et al. (2003) J. Clin. Microbiol. vol. 41 pp 1856-60; Whelan et al. (2003) Infect. Immun. vol 71 pp 6420-5). When comparing cellular responses induced by recombinant protein antigens, the presence of contamination endotoxin should also be considered. However, it is unlikely that immunomodulation from possible endotoxin contamination can explain the potent responses to the protein antigens in the current study, since skin-reactions were also induced by the synthetic polypeptides which are endotoxin-free.

Pollock et al. also demonstrated that PPD-induced bovine skin reactions were maximal at 72 hours whilst the response to ESAT-6 was often greatest at 96 hours (Pollock et al. (2003) J. Clin. Microbiol. vol. 41 pp 1856-60). The present data confirmed 72 hours to be optimal for the measurement of the SICCT response (FIG. 1) and increases in the protein-cocktail responder frequency were also observed when reactions were read at 96 or 120 hours, such that responder frequency increased from 29/37, to 31/37 and then 32/37 for the 72, 96 and 120 hour time-points respectively. However, the increase in responder frequency was not significant (data not shown) and there was no increase in the magnitude of comparative responses. Since highly specific reactions were observed in the majority of animals at 72 hours using the optimised defined cocktails, measuring responses at this time point has the practical benefit of allowing the option of testing defined antigens and PPD in parallel and then reading the reaction on the same day.

Although the present invention has been described with reference to exemplary embodiments, those skilled in the art will recognise that various modifications and variations to the same can be accomplished without departing from the spirit and scope of the present invention and that such modifications are clearly contemplated herein. No limitation with respect to the specific embodiments disclosed herein and set forth in the appended claims is intended nor should any be inferred.

All documents cited herein are incorporated by reference in their entirety.

The invention claimed is:

1. A method for detecting *Mycobacterium bovis* or *Mycobacterium tuberculosis* infection in an animal comprising the steps of:

(a) selecting an administration site on the skin of an animal;

(b) measuring the skin induration at the site to determine skin thickness;

(c) interdermally administering at the administration site a skin test diagnostic reagent comprising at least one CFP-10 epitope polypeptide, at least one ESAT-6 epitope polypeptide and at least one Rv3615c epitope polypeptide, characterised in that the reagent elicits a positive result at the administration site when administered in a skin test to an animal infected with *Mycobacterium bovis* or *Mycobacterium tuberculosis;*

(d) measuring the skin induration at the administration site 72 hours after completion of step (c) to determine skin thickness, optionally also at 96 hours and 120 hours after completion of step (c);

(e) determining the difference in skin thickness between the measurements from steps (b) and (d);

(f) wherein an animal showing increased skin thickness in step (d) compared to step (b) is identified as being infected with *Mycobacterium bovis* or *Mycobacterium tuberculosis.*

2. The method according to claim 1, wherein said reagent comprises one or more of the polypeptides having amino acid sequences SEQ ID NOs:35, 36 and 38.

3. The method according to claim 1, wherein said reagent comprises one or more polypeptides having amino acid sequences SEQ ID NOs:1-10.

4. The method according to claim 1, wherein said reagent comprises one or more polypeptides having amino acid sequences SEQ ID NOs:11-21.

5. The method according to claim 1, wherein said reagent comprises one or more polypeptides having amino acid sequences SEQ ID NOs:23-34.

6. The method according to claim 1, wherein said reagent further comprises at least one MPB83 epitope polypeptide.

7. The method according to claim 6, wherein said reagent comprises a polypeptide having amino acid sequence SEQ ID NO:37.

8. The method according to claim 6, wherein said reagent comprises a polypeptide having amino acid sequence SEQ ID NO:22.

9. The method according to claim 1, wherein said reagent comprises at least one polypeptide having amino acid sequence SEQ ID NO:33 or 34.

10. The method according to claim 1, wherein said reagent comprises the polypeptides having amino acid sequences SEQ ID NOs:31, 32 and 34.

11. The method according to claim 1, wherein said reagent comprises the polypeptides having amino acid sequence SEQ ID NOs:23-33.

12. The method according to claim 1, wherein said reagent comprises the polypeptides having amino acid sequence SEQ ID NOs:23-34.

13. The method of claim 1, wherein the diagnostic reagent is in liquid form and is in at least one aliquot of 0.05-0.15 ml comprising 1-15 μg of each polypeptide.

14. The method according to claim 13, wherein the diagnostic reagent is able to differentiate between a *Mycobacterium bovis* or *Mycobacterium tuberculosis* infected mammal and a mammal vaccinated against infection by a *Mycobacterium bovis* or *Mycobacterium tuberculosis.*

15. The method according to claim 13, wherein each aliquot is contained in a disposable injection device.

16. The method of claim 1, wherein the diagnostic reagent is in liquid form and is in at least one aliquot of 0.1 ml comprising 10 μg of each polypeptide.

17. A method for detecting *Mycobacterium bovis* or *Mycobacterium tuberculosis* infection in an animal comprising (a) measuring the skin induration at skin test site to determine skin thickness prior to injection;

(b) interdermally injecting a skin test diagnostic reagent comprising at least one CFP-10 epitope polypeptide, at least one ESAT-6 epitope polypeptide and at least one Rv3615c epitope polypeptide, characterised in that the reagent elicits a positive result when administered in a skin test to an animal infected with *Mycobacterium bovis* or *Mycobacterium tuberculosis* at the skin test site;

(c) measuring the skin induration at the injection site 72-120 hours after completion of step (b) to determine skin thickness;

(d) determining the difference in skin thickness between the measurements from steps (a) and (c);

wherein an animal showing increased skin thickness in step (c) compared to step (a) is identified as being infected with *Mycobacterium bovis* or *Mycobacterium tuberculosis.*

18. The method of claim 17, wherein the diagnostic reagent is in liquid form and included is in at least one aliquot of 0.05-0.15 ml comprising 1-15 μg of each polypeptide.

19. The method of claim 17, wherein the diagnostic reagent elicits significant skin thickening in animals infected with *Mycobacterium bovis* or *Mycobacterium tuberculosis.*

20. The method of claim 17, wherein the diagnostic reagent does not elicit significant skin thickening in animals vaccinated against *Mycobacterium bovis* or *Mycobacterium tuberculosis.*

21. The method of claim 17, wherein the diagnostic reagent is in liquid form and is in at least one aliquot of 0.1 ml comprising 10 μg of each polypeptide.

* * * * *